(12) United States Patent
Dell et al.

(10) Patent No.: US 9,925,013 B2
(45) Date of Patent: Mar. 27, 2018

(54) SYSTEM AND METHOD FOR CONFIGURING POSITIONS IN A SURGICAL POSITIONING SYSTEM

(71) Applicant: Synaptive Medical (Barbados) Inc., Bridgetown (BB)

(72) Inventors: Trevor James Dell, Toronto (CA); Adam Keith White, Toronto (CA); David Bruce McFadzean, Toronto (CA); Monroe Milas Thomas, Toronto (CA); Oleg Valerievitch Rakitine, Toronto (CA); Mark Leon Unger, Toronto (CA); Kirusha Srimohanarajah, Toronto (CA); Gal Sela, Toronto (CA); Kamyar Abhari, Toronto (CA); Bradley Allan Fernald, Toronto (CA); William Dennis Babby, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 107 days.

(21) Appl. No.: 14/995,826

(22) Filed: Jan. 14, 2016

(65) Prior Publication Data

US 2017/0202628 A1    Jul. 20, 2017

(51) Int. Cl.
*G06F 19/00*    (2011.01)
*A61B 34/32*    (2016.01)
(Continued)

(52) U.S. Cl.
CPC .............. *A61B 34/32* (2016.02); *A61B 34/20* (2016.02); *A61B 90/361* (2016.02); *A61B 90/11* (2016.02);
(Continued)

(58) Field of Classification Search
None
See application file for complete search history.

(56) References Cited

U.S. PATENT DOCUMENTS 5,436,542 A * 7/1995 Petelin ................... B25J 9/1679
                                                    318/567
5,524,180 A * 6/1996 Wang .................. B60R 21/0132
                                                    600/117

(Continued)

OTHER PUBLICATIONS

Universal Robots (UR5) User's Manual, Version 3, 2014.

*Primary Examiner* — Bhavesh V Amin
(74) *Attorney, Agent, or Firm* — Ridout & Maybee LLP

(57) ABSTRACT

A medical navigation system is provided including a surgical positioning system for positioning a payload during a medical procedure. The medical navigation system has a robotic arm having a plurality of joints, the robotic arm forming part of the surgical positioning system and having an end effector for holding the payload, an input device for providing input, and a controller electrically coupled to the robotic arm and the input device. The controller has a processor coupled to a memory and the controller is configured to perform the following during the medical procedure: position the robotic arm in a first position by providing a first positioning signal to the robotic arm; save the first position in the memory as a first saved position in response to a signal received from the input device; position the robotic arm in a second position by providing a second positioning signal to the robotic arm; and return the robotic arm to the first position by loading the first saved position from the memory and providing the first positioning signal to the robotic arm when an input is received from the input device corresponding to a command to return to the first saved position.

17 Claims, 9 Drawing Sheets

(51) Int. Cl.
*A61B 34/20* (2016.01)
*A61B 90/00* (2016.01)
*A61B 90/11* (2016.01)

(52) U.S. Cl.
CPC .............. *A61B 2034/2055* (2016.02); *A61B 2034/2074* (2016.02); *A61B 2090/363* (2016.02)

(56) References Cited

U.S. PATENT DOCUMENTS

| | | | |
|---|---|---|---|
| 5,553,198 A * | 9/1996 | Wang ................ | A61B 34/70 606/19 |
| 5,657,429 A * | 8/1997 | Wang ................ | A61B 34/70 600/118 |
| 5,754,741 A * | 5/1998 | Wang ................ | A61B 34/70 600/417 |
| 5,799,661 A * | 9/1998 | Boyd ............... | A61B 17/00234 128/898 |
| 6,001,108 A | 12/1999 | Wang et al. | |
| 6,120,433 A * | 9/2000 | Mizuno ............. | A61B 34/70 600/102 |
| 6,228,089 B1 | 5/2001 | Wahrburg | |
| 6,642,686 B1 | 11/2003 | Ruch | |
| 8,386,077 B2 | 2/2013 | Birkenbach et al. | |
| 9,168,153 B2 * | 10/2015 | Bettenga ............ | A61F 2/46 |
| 2003/0208187 A1 * | 11/2003 | Layer ................ | A61B 90/11 606/1 |
| 2005/0193451 A1 | 9/2005 | Quistgaard et al. | |
| 2007/0021738 A1 * | 1/2007 | Hasser ............... | A61B 8/4218 606/1 |
| 2007/0055144 A1 * | 3/2007 | Neustadter .......... | A61N 5/1049 600/425 |
| 2009/0036902 A1 * | 2/2009 | DiMaio ............. | A61B 19/2203 606/130 |
| 2010/0135554 A1 * | 6/2010 | Kohlmann ......... | G06T 19/00 382/128 |
| 2010/0174410 A1 * | 7/2010 | Greer ............... | B25J 9/1671 700/264 |
| 2011/0040305 A1 * | 2/2011 | Gomez ............. | A61B 19/2203 606/130 |
| 2011/0118753 A1 * | 5/2011 | Itkowitz ............ | G06F 3/014 606/130 |
| 2012/0022696 A1 * | 1/2012 | Aoussat ............. | A61B 34/74 700/275 |
| 2012/0101508 A1 * | 4/2012 | Wook Choi ........ | B25J 9/1697 606/130 |

* cited by examiner

SYSTEM AND METHOD FOR CONFIGURING POSITIONS IN A SURGICAL POSITIONING SYSTEM

TECHNICAL FIELD

The present disclosure is generally related to image guided medical procedures, and more specifically to a system and method for configuring positions in a surgical positioning system.

BACKGROUND

The present disclosure is generally related to image guided medical procedures using a surgical instrument, such as an optical scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon is aware of what is transpiring in the operating room, has a proper view of the surgical site of interest, and has proper control of the surgical positioning system without undue distraction.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12. Optical tracking systems, used in the medical procedure, track the position of a part of the instrument that is within line-of-site of the optical tracking camera. The surgical positioning system will often have a camera mounted thereon and is responsible for maintaining a view of the surgical site of interest by moving the camera to the proper positions, under the control of the surgeon.

During surgical procedures, a surgeon utilizing an external optical system may want or need to view the surgical site from multiple angles. A problem can occur if it takes a significant amount of time to achieve this or if the surgeon needs to remove tools from the surgical field to move the optical system between these different angles. In many cases, these viewing angles are known before the procedure or can all be defined at the start of the procedure.

Conventional systems have not offered good solutions for ensuring that a surgeon has a good view of the surgical site without constantly having to reconfigure the optical system positioning the camera. It would be desirable to have a system that helps a surgeon maintain the optical system in the appropriate positions without placing undue burden on the surgeon during the medical procedure.

SUMMARY

One aspect of the present disclosure provides a medical navigation system including a surgical positioning system for positioning a payload during a medical procedure. The medical navigation system has a robotic arm having a plurality of joints, the robotic arm forming part of the surgical positioning system and having an end effector for holding the payload, an input device for providing input, and a controller electrically coupled to the robotic arm and the input device. The controller has a processor coupled to a memory and the controller is configured to perform the following during the medical procedure: position the robotic arm in a first position by providing a first positioning signal to the robotic arm; save the first position in the memory as a first saved position in response to a signal received from the input device; position the robotic arm in a second position by providing a second positioning signal to the robotic arm; and return the robotic arm to the first position by loading the first saved position from the memory and providing the first positioning signal to the robotic arm when an input is received from the input device corresponding to a command to return to the first saved position.

Another aspect of the present disclosure provides a method of positioning a payload during a medical procedure in a medical navigation system including a surgical positioning system. The medical navigation system has a robotic arm, an input device, and a controller. The robotic arm has a plurality of joints and forms part of the surgical positioning system and has an end effector for holding the payload. The controller has a processor coupled to a memory, the method comprising: positioning the robotic arm in a first position; saving the first position in the memory as a first saved position in response to a signal received from the input device; positioning the robotic arm in a second position; and returning the robotic arm to the first position by loading the first saved position from the memory when an input is received from the input device corresponding to a command to return to the first saved position.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
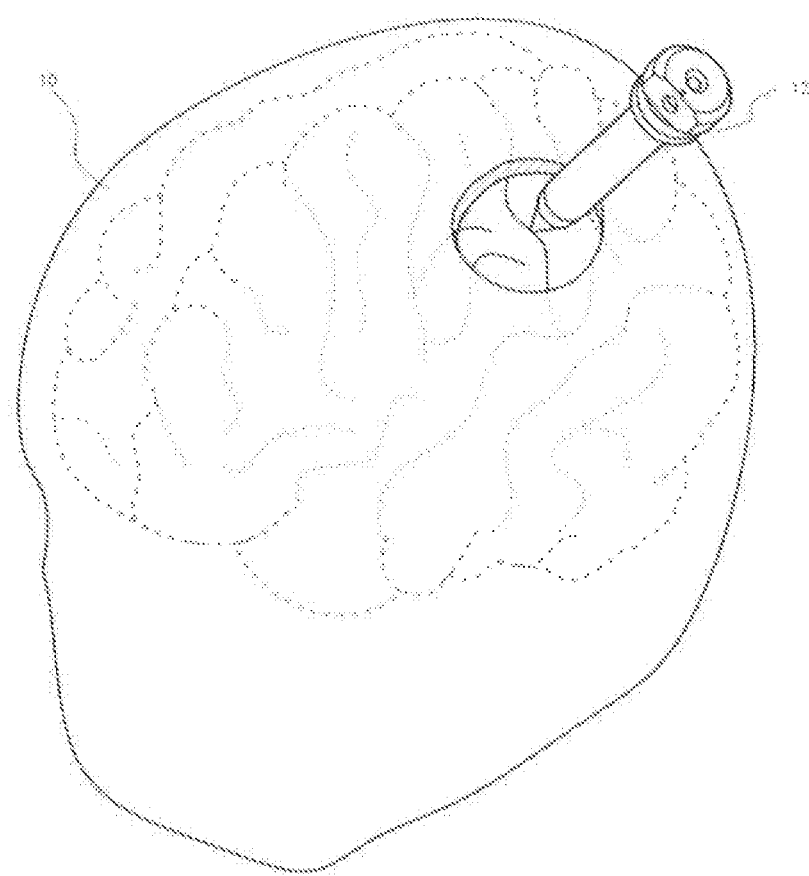
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g., minimally invasive medical procedures) are performed based on access to internal tissue through the access port.

Figure 2:
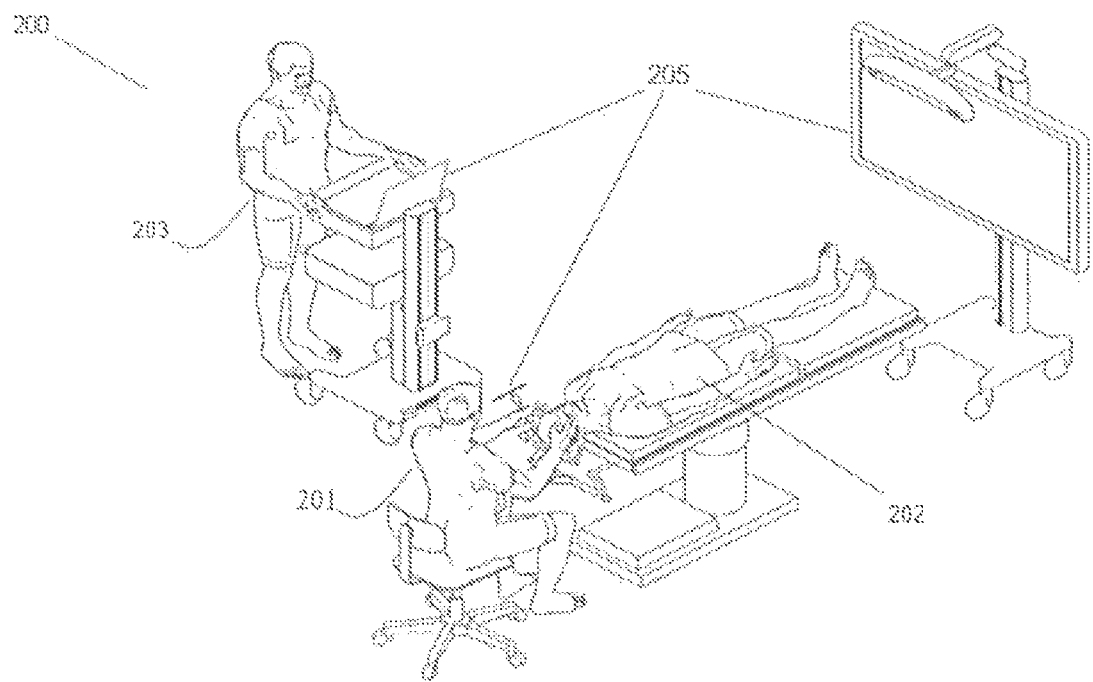
FIG. 2 shows an exemplary navigation system to support minimally invasive surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
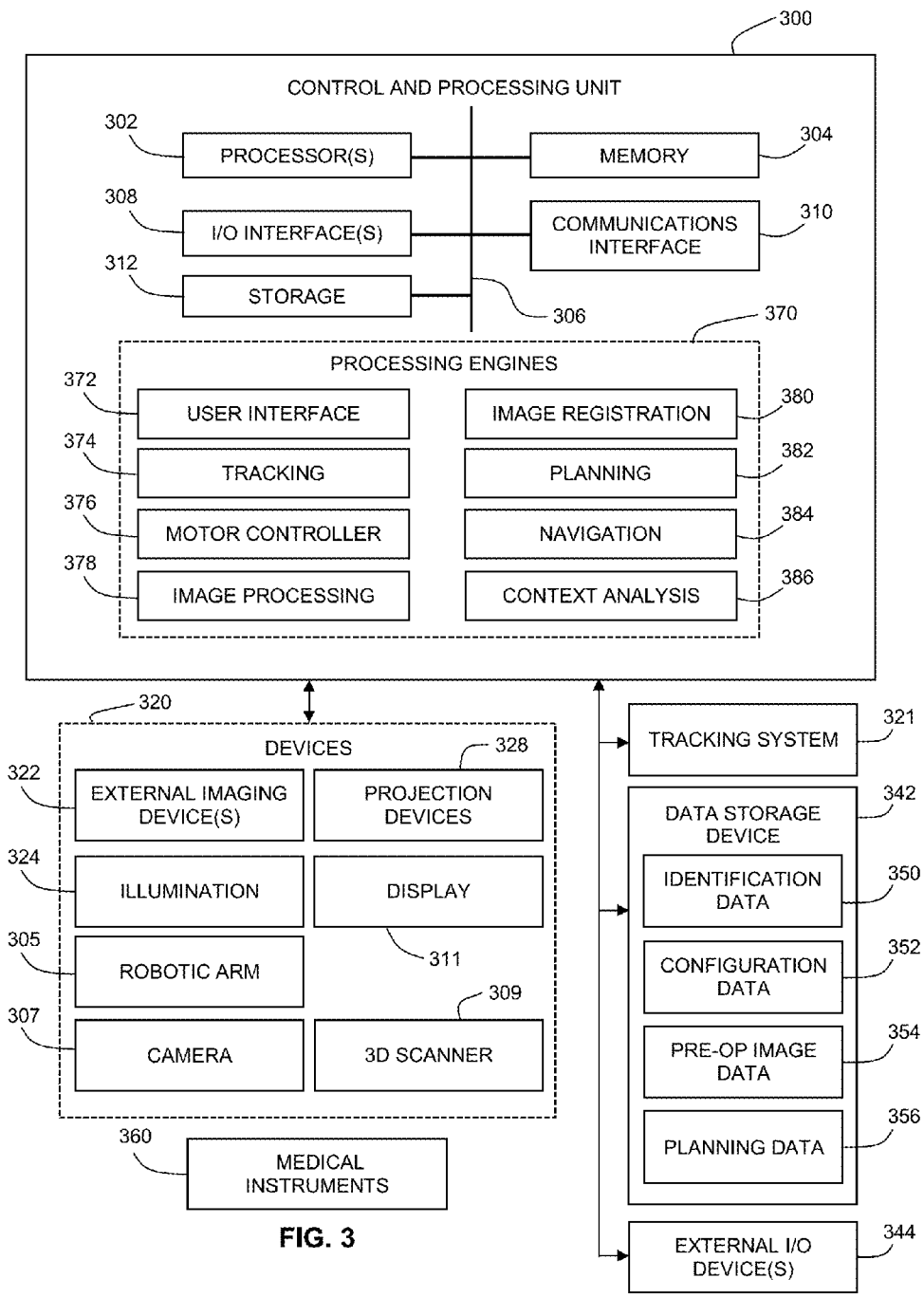
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300. In another example, camera 307 may be a video camera.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, and one or more displays 311, and a scanner 309, which in one example may be a three dimensional (3D) scanner.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370. In some examples, the set of processing engines (370) may reside on a plurality of independent control and processing units (300), connected via a network, where the devices (320) may be distributed between the set of control and processing units (300), as well as the data device storage (342).

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, laparoscopic surgery, etc. While several examples have been provided, aspects of the present disclosure may be applied to any suitable medical procedure.

Figure 4A:
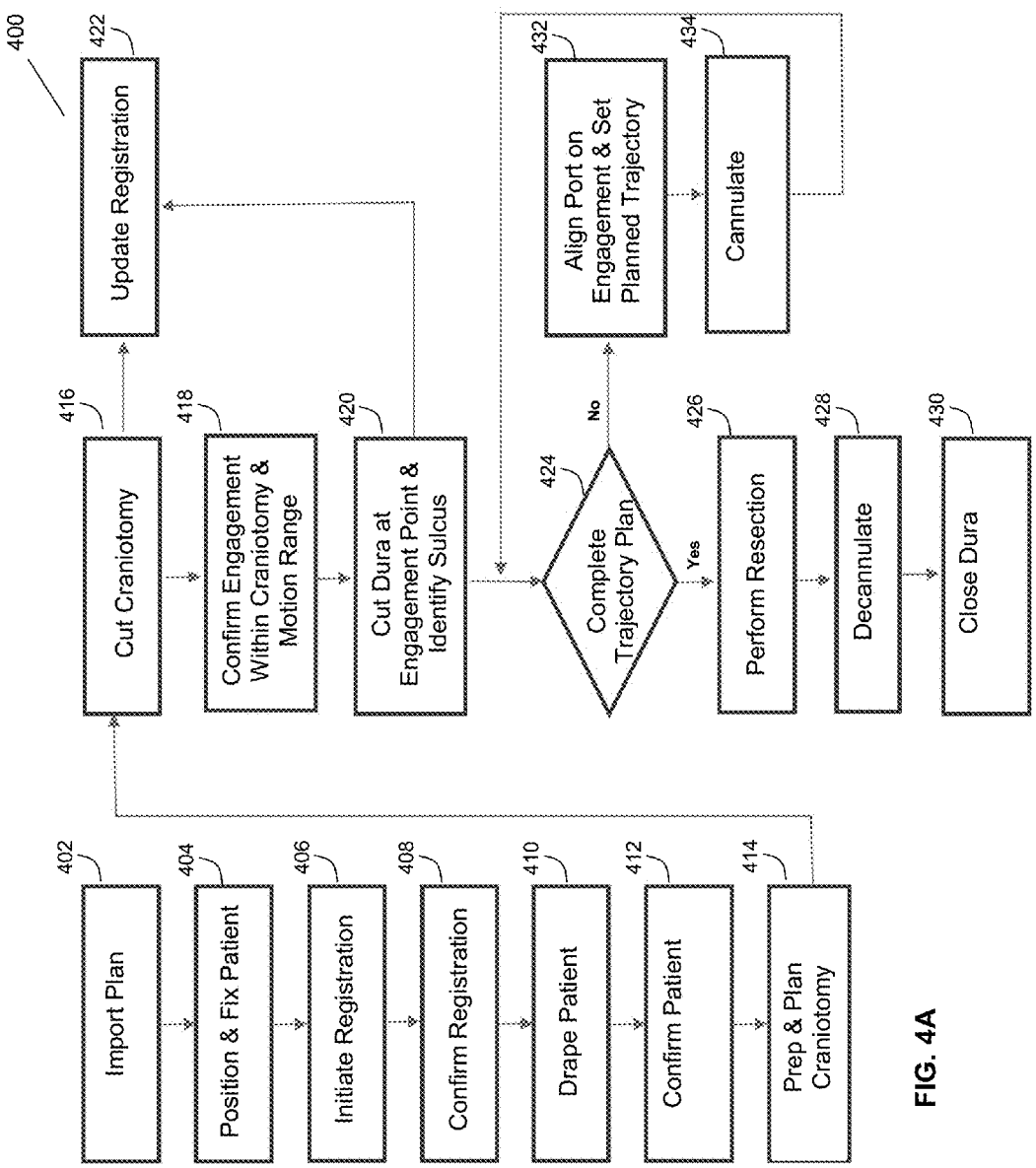
FIG. 4A is a flow chart illustrating a method involved in a surgical procedure using the navigation system of FIG. 2.

Referring to FIG. 4A, a flow chart is shown illustrating a method 400 of performing a surgical procedure using a navigation system, such as the medical navigation system 205 described in relation to FIG. 2. At a first block 402, the surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower of medical navigation system 205.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
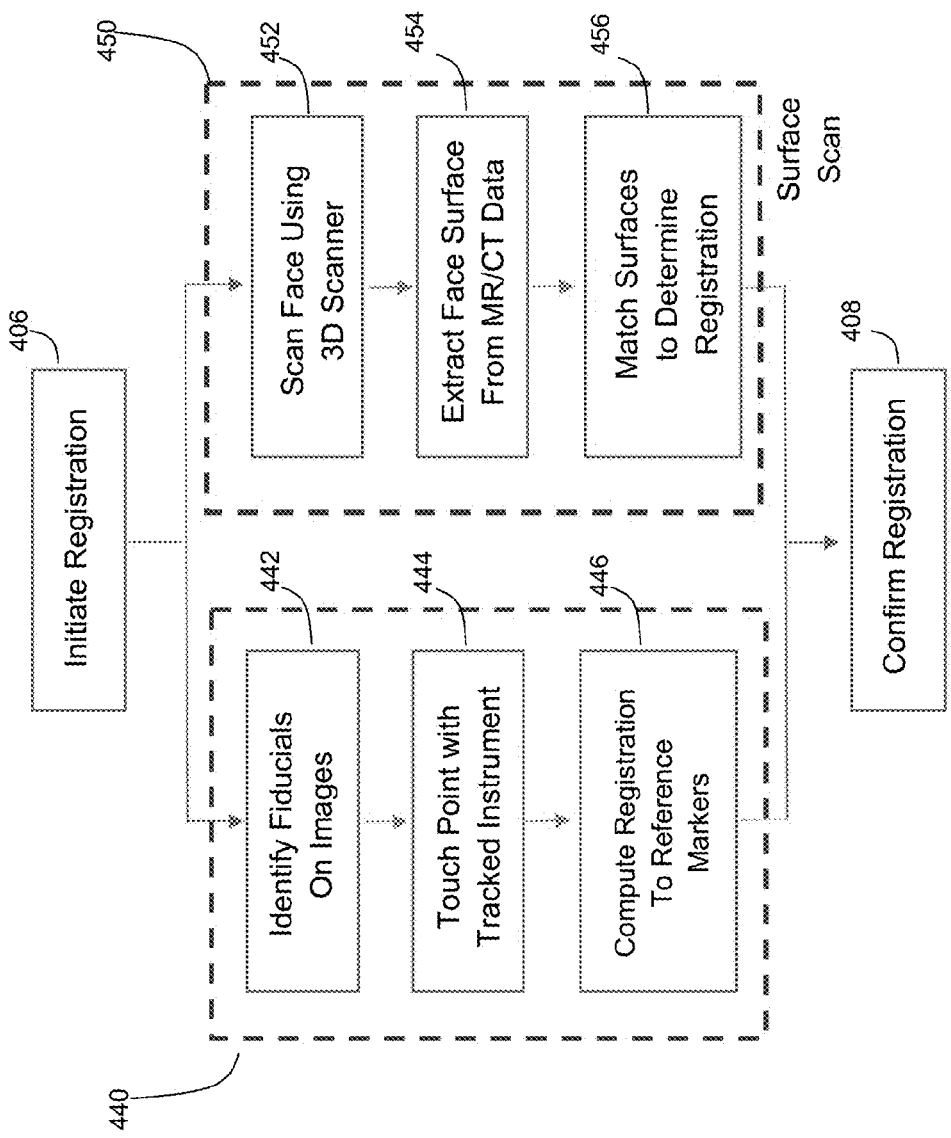
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4B.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
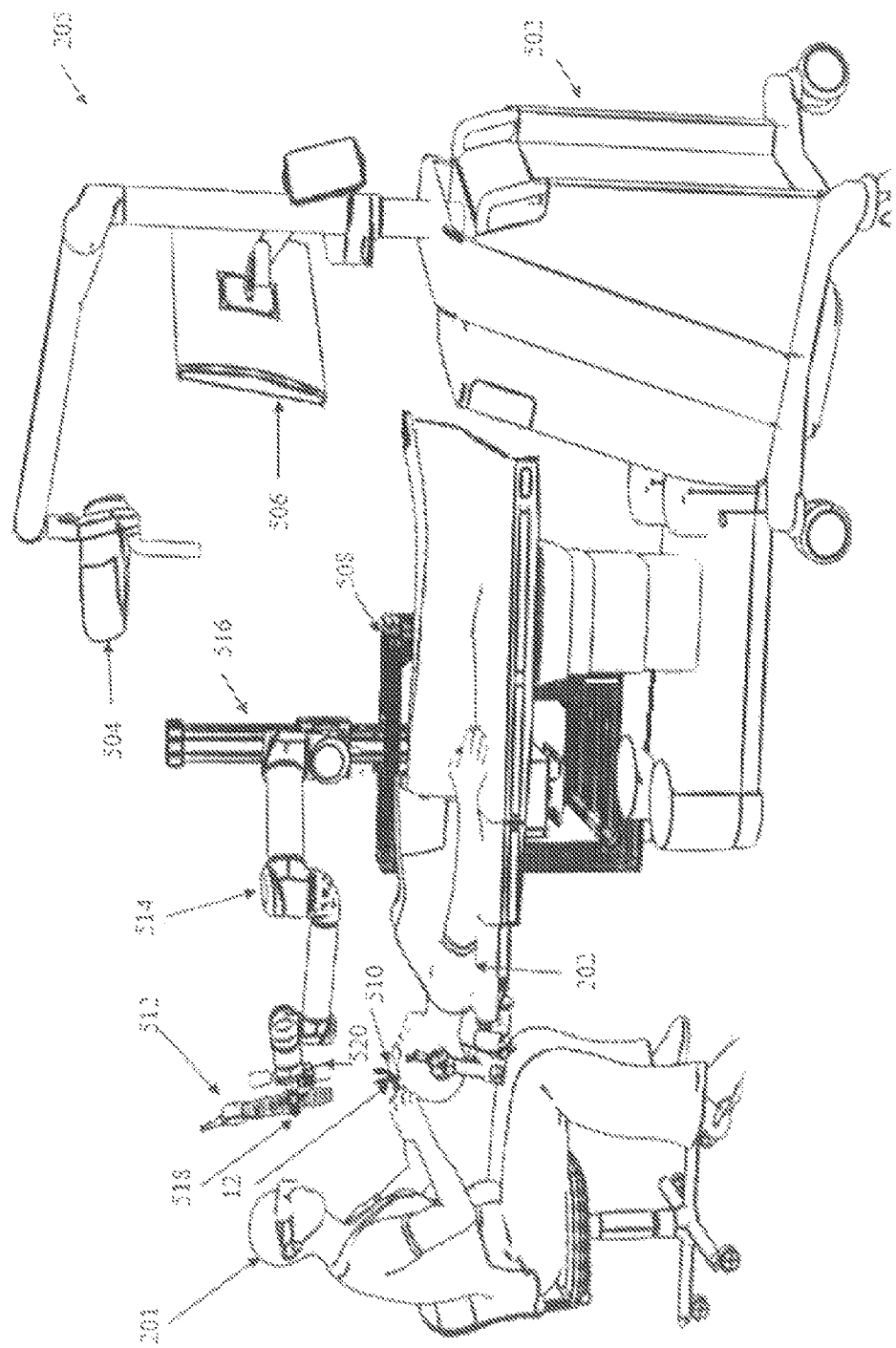
FIG. 5 is an exemplary navigation system similar to FIG. 2 illustrating system components of an exemplary surgical system that may be used for configuring positions of the surgical system.

FIG. 5 is a diagram illustrating components of an exemplary surgical system that is similar to FIG. 2. FIG. 5 illustrates a navigation system 205 having an equipment tower 502, tracking system 504, display 506, an intelligent positioning system 508 and tracking markers 510 used to tracked instruments or an access port 12. Tracking system 504 may also be considered an optical tracking device, tracking camera, video camera, 3D scanner, or any other suitable camera or scanner based system. In FIG. 5, a surgeon 201 is performing a tumor resection through a port 12, using an imaging device 512 (e.g., a scope and camera) to view down the port at a sufficient magnification to enable enhanced visibility of the instruments and tissue. The imaging device 512 may be an external scope, videoscope, wide field camera, or an alternate image capturing device. The imaging sensor view is depicted on the visual display 506 which surgeon 201 uses for navigating the port's distal end through the anatomical region of interest.

An intelligent positioning system 508 comprising an automated arm 514, a lifting column 516 and an end effector 518, is placed in proximity to patient 202. Lifting column 516 is connected to a frame of intelligent positioning system 508. As seen in FIG. 5, the proximal end of automated mechanical arm 514 (further known as automated arm 514 herein) is connected to lifting column 516. In other embodiments, automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

End effector 518 is attached to the distal end of automated arm 514. End effector 518 may accommodate a plurality of instruments or tools that may assist surgeon 201 in his procedure. End effector 518 is shown as holding an external scope and camera, however it should be noted that this is merely an example and alternate devices may be used with the end effector 518 such as a wide field camera, microscope and OCT (Optical Coherence Tomography), video camera, 3D scanner, or other imaging instruments. In another example, multiple end effectors may be attached to the distal end of automated arm 518, and thus assist the surgeon 201 in switching between multiple modalities. For example, the surgeon 201 may want the ability to move between microscope, and OCT with stand-off optics. In a further example, the ability to attach a second, more accurate, but smaller range end effector such as a laser based ablation system with micro-control may be contemplated.

In one example, the intelligent positioning system 508 receives as input the spatial position and pose data of the automated arm 514 and target (for example the port 12) as determined by tracking system 504 by detection of the tracking markers on the wide field camera on port 12. Further, it should be noted that the tracking markers may be used to track both the automated arm 514 as well as the end effector 518 either collectively or independently. It should be noted that a wide field camera 520 is shown in FIG. 5 and that it is connected to the external scope (e.g., imaging device 512) and the two imaging devices together are held by the end effector 518. It should additionally be noted that although these are depicted together for illustration of the diagram that either could be utilized independently of the other, for example where an external video scope can be used independently of the wide field camera 520.

Intelligent positioning system 508 computes the desired joint positions for automated arm 514 so as to maneuver the end effector 518 mounted on the automated arm's distal end to a predetermined spatial position and pose relative to the port 12. This redetermined relative spatial position and pose is termed the "Zero Position" where the sensor of imaging device 512 and port 12 are axially aligned.

Further, the intelligent positioning system 508, optical tracking device 504, automated arm 514, and tracking markers 510 may form a feedback loop. This feedback loop works to keep the distal end of the port 12 (located inside the brain) in constant view and focus of the end effector 518 given that it is an imaging device as the port position may be dynamically manipulated by the surgeon during the procedure. Intelligent positioning system 508 may also include a foot pedal for use by the surgeon 201 to align the end effector 518 (i.e., holding a videoscope) of automated arm 514 with the port 12. Ensuring that the imaging device 512 and/or wide field camera 520 remain focused on the surgical site of interest without unduly interfering with the surgeon during the medical procedure is one of the objectives of the present application and is discussed in more detail below, particularly in connection with FIGS. 7 and 8.

Figure 6:
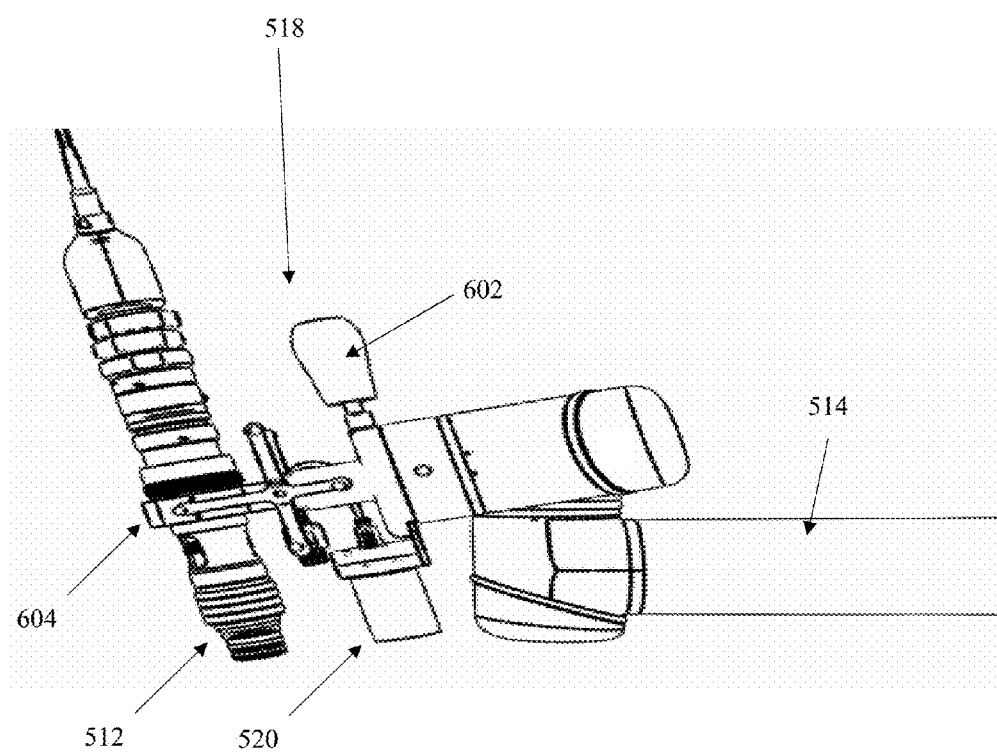
FIG. 6 is perspective drawing illustrating a conventional end effector holding a camera.

Referring to FIG. 6, a conventional end effector 518 is shown attached to automated arm 514. The end effector 518 includes a handle 602 and a scope clamp 604. The scope clamp 604 holds imaging device 512. The end effector also has wide field camera 520 attached thereto, which in one example could be a still camera, video camera, or 3D scanner used to monitor muscles of the patient for movement, tremors, or twitching.

One aspect of the present disclosure provides a stored position function that focuses on the reality that there are some arm positions that will be constant throughout most procedures and are unlikely to change often. These constant positions can relate to draping, automated arm 514 orientation positions (e.g., left or right sided), storage positions, shipping positions, etc. These constant positions may be used before and/or after a surgical procedure and this feature may be controlled via a user interface, a foot pedal, voice control, etc. In one example, these constant positions may be stored as a list of joint angles pertaining to the arm configuration that is related to that particular position, since the automated arm 514 has a number of joints with an encoder associated with each joint. In one example, the automated arm 514 may have six joints or even more. However, the automated arm 514 may have any number of joints according to the design criteria of a particular application. In one example, the automated arm 514 may go to a known position when the automated arm 514 is started up and may be configured to toggle between different positions of interest.

In another example, the interface of the automated arm 514 may provide the user with an undo function and a redo function. During a medical procedure, the surgeon may wish to undo or redo automated arm 514 movements or positions. This feature may both be used to correct an undesired movement of the automated arm 514 or to revisit a previous position that is clinically relevant. The undo and redo positions may be stored as a list of joint angles pertaining to sequential moves in a movement stack, for example saved in the memory 304 of control and processing unit 300 (FIG. 3). The undo and redo feature may be used during a procedure but may also be useful during setup and wrap up of a medical procedure. The undo and redo feature may be controlled via a foot pedal, or by other sources of control such as a user interface, voice control, etc. In one example, when a successful move is made using the automated arm 514, the surgeon may be provided with the option to save the move in the memory 304, where the joint angles are saved. In one example, the joint angles may be saved relative in space to a patient reference based on a trajectory set in the procedure plan or guide.

Another aspect of the present application provides for a dynamic memory position. During a procedure, the surgeon may wish to dynamically save automated arm 514 movements so that the movements can be revisited at a later time during the same procedure. In one example, the dynamic memory positions may be stored as joint angles pertaining to the saved automated arm 514 position. In another example, the dynamic memory positions may be stored relative to an external frame of reference, such as the patient.

The dynamic memory position feature may be mainly used during a procedure as dynamically stored positions but may not be as useful in the setup and wrap up phases of the procedure. In one example, the dynamic memory position feature may be controlled via a foot pedal, user interface, voice control, etc. Further, the present application provides for dynamic allocation of pedal mapping, where a foot pedal may be allocated to trigger the undo feature instead of requiring such input on a user interface of the control and processing unit 300. In one example, stored positions may be recreated by aligning to tools that are held in the same position from when the desired position was first stored.

Another aspect of the present application provides for surgeons to set stored positions of the automated arm 514 during a medical procedure. These stored positions often provide various perspectives on the surgical field. Conventionally, a surgeon would have to verbally relay his or her desire to save the current automated arm 514 position to the clinical applications specialist (e.g., the operator 203 in FIG. 2) who is assisting with manipulating the controls of the medical navigation system 205. When a surgeon wants the automated arm 514 to move to one of the stored positions, the surgeon tries to recall the number that the specialist had given that stored position or tries to describe the view for the specialist to remember which one it was. This additional dialog introduces another barrier for changing the position of automated arm 514, leading to additional time being spent clarifying the view. Miscommunication between the surgeon and operator would lead to the automated arm 514 going into a position that the surgeon did not intend. In this case time is unnecessarily wasted and the surgeon's workflow and concentration would be broken. In fact, communication error in the operating room is one of the main sources of surgical failures, jeopardizing patient safety. In one example, this problem may be addressed by streaming stored position view data to an augmented viewport, such that the surgeon is able to see virtual renderings of some or all of the available stored positions. The virtual renderings may also include sample snapshots that were taking using the optics systems such as cameras at that particular stored position. The virtual renderings may be shown on a display, augmented reality goggles, etc.

Figure 7:
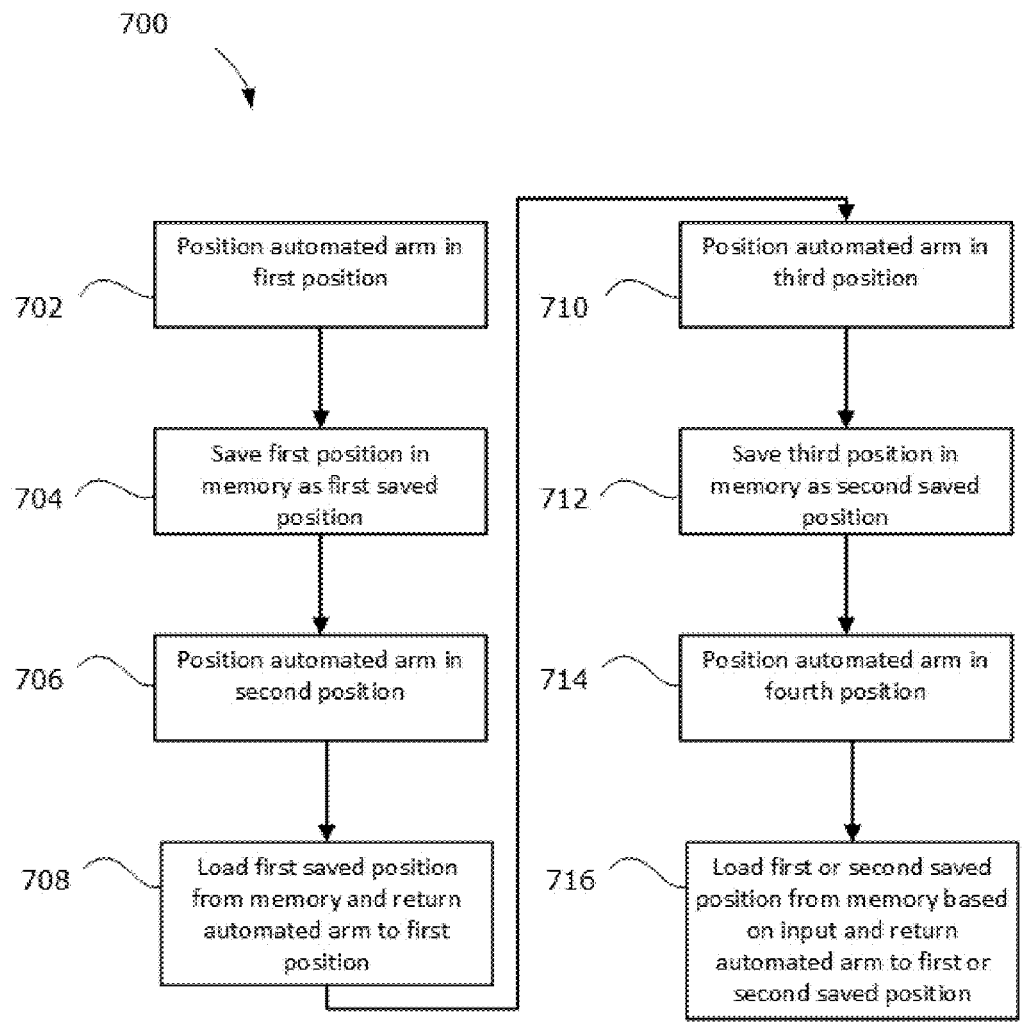
FIG. 7 is a flow chart is illustrating a method of configuring positions in a surgical positioning system according to one aspect of the present description.

Referring now to FIG. 7, a flow chart is showing illustrating a method 700 of configuring positions in a surgical positioning system according to one aspect of the present description. The method 700 may be executed on a medical navigation system, such as the navigation system 205 (FIG. 2) that includes the control and processing unit 300 (FIG. 3), which may also include a surgical positioning system, such as intelligent positioning system 508 (FIG. 5), for positioning a payload during a medical procedure. The medical navigation system includes a robotic arm, such as automated arm 514, having a plurality of joints. The robotic arm forms part of the surgical positioning system and has an end effector for holding the payload, such as end effector 518 (FIGS. 5 and 6). The medical navigation system further has an input device for providing input and a controller (e.g., control and processing unit 300) electrically coupled to the robotic arm and the input device. The controller may have a processor (e.g., processor 302) coupled to a memory (e.g., memory 304). The controller may be configured to perform the method 700.

At a first block 702, the robotic arm (e.g., the automated arm 514) is positioned in a first position by providing a first positioning signal to the robotic arm. The robotic arm may be placed in the first position either under control of the navigation system 205 where a user is providing an associated input such as through a graphical user interface, a foot pedal, a voice command, or any other suitable input, or the surgeon may simply grab the robotic arm and manually position the robotic arm in the first position.

Next, at a block 704, the first position is saved in the memory as a first saved position in response to a signal received from the input device. The first position may be saved in response to a control of the navigation system 205 where a user is providing an associated input such as through a graphical user interface, a foot pedal, a voice command, or any other suitable input.

Next, at a block 706, the robotic arm (e.g., the automated arm 514) is positioned in a second position by providing a second positioning signal to the robotic arm. The robotic arm may be placed in the second position either under control of the navigation system 205 where a user is providing an associated input such as through a graphical user interface, a foot pedal, a voice command, or any other suitable input, or the surgeon may simply grab the robotic arm and manually position the robotic arm in the second position.

Next, at a block 708, the robotic arm may be returned to the first position by loading the first saved position from the memory and providing the first positioning signal to the robotic arm when an associated input is received from the input device corresponding to a command to return to the first saved position. The input device may include a keyboard or mouse connected to the navigation system 205. Input may be provided, such as through a graphical user interface, a foot pedal, a voice command, or any other suitable input.

In one example, the first saved position may be defined by encoder joint angles that are saved, where one angle is saved for each encoder associated with each of the plurality of joints. In one example, the automated arm may have six degrees of freedom, six joints, and six associated encoders. However, any suitable number of joints and encoders may be used according to the design criteria of a particular application.

In one example, the input device may include any of a foot pedal, a microphone providing voice input, a touch sensitive overlay on the display, a mouse, and/or a keyboard. In one example, the payload includes a camera held by the end effector, such as the camera 307, 512, or 520, and electrically coupled to the controller, or a surgical tool held by the end effector.

In one example, the first position is manually positioned a first time based on input provided to the medical navigation system. The input may include a surgeon physically moving the robotic arm to the first position or the surgeon moving the robotic arm to the first position by providing input using the input device.

Returning to FIG. 7, at a block 710, the robotic arm (e.g., the automated arm 514) is positioned in a third position by providing a third positioning signal to the robotic arm. The robotic arm may be placed in the third position either under control of the navigation system 205 where a user is providing an associated input such as through a graphical user interface, a foot pedal, a voice command, or any other suitable input, or the surgeon may simply grab the robotic arm and manually position the robotic arm in the first position.

Next, at a block 712, the third position is saved in the memory as a second saved position in response to a signal received from the input device. The third position may be saved in response to a control of the navigation system 205 where a user is providing an associated input such as through a graphical user interface, a foot pedal, a voice command, or any other suitable input.

Next, at a block 714, the robotic arm (e.g., the automated arm 514) is positioned in a fourth position by providing a fourth positioning signal to the robotic arm. The robotic arm may be placed in the fourth position either under control of the navigation system 205 where a user is providing an associated input such as through a graphical user interface, a foot pedal, a voice command, or any other suitable input, or the surgeon may simply grab the robotic arm and manually position it in the fourth position.

Next, at a block 716, the robotic arm may be returned to either the first saved position or the second saved position by loading the first saved position or the second saved from the memory and providing either the first or second positioning signal to the robotic arm when an associated input is received from the input device corresponding to a command to return to the first or second saved position. The input device may include a keyboard or mouse connected to the navigation system 205, input such as through a graphical user interface, a foot pedal, a voice command, or any other suitable input.

In one example, each of the first and second saved positions corresponds to a tool held by the end effector and the controller may be further configured to automatically position the robotic arm in one of the first and second saved positions when the corresponding tool is placed in the end effector. For example, if a probe is placed in the end effector, the navigation system 205 may automatically identify that the probe is in the end effector and automatically go to a corresponding position, such as the first saved position. Any saved position may correspond to any suitable tool, depending on the design criteria of a particular application and any user input to the navigation system 205.

While the example of a first and second saved position is provided above, any suitable number of saved positions may be used according to the requirements of the procedure being performed with the medical navigation system 205.

In another example, the medical navigation system 205 may have a tracking system (e.g., tracking system 321 interfacing with devices such as camera 307 or 3D scanner 309) electrically coupled to the controller. The first saved position or the second saved position may be defined relative to a position of a patient determined by the tracking system. The tracking system may be an optical tracking system having a camera for viewing optical tracking markers attached to the patient, a 3D scanning tracking system having a 3D scanner for tracking the patient, an electromagnetic tracking system having an electromagnetic sensor for tracking electromagnetic markers on the patient, or any other suitable type of tracking system.

In yet another example, stored positions may automatically propagate and be saved, at least temporarily, from a preplanned trajectory from the navigation system 205 when using a tracking camera and patient reference. In another example, when the robotic arm is automatically following a trajectory based on the reference to the patient, at least some of the significant positions along this trajectory may automatically be saved as stored positions for use later in the procedure.

Figure 8:
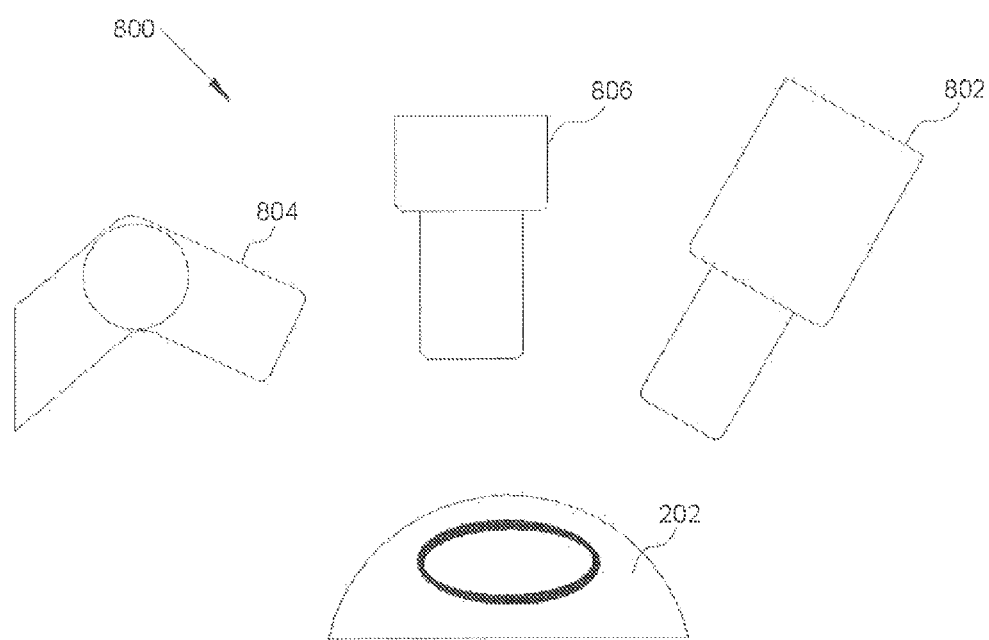
FIG. 8 is a block diagram illustrating an example of a virtual reality component according to one aspect of the present description.

Referring now to FIG. 8, a block diagram is shown illustrating an example of a virtual reality component view 800 according to one aspect of the present description. In one example, the medical navigation system 205 may have an augmented reality component for providing a view of saved positions including the first saved position to a surgeon, thereby allowing the surgeon to easily select between saved positions. As shown in FIG. 8, a head of the patient 202 is shown. Relative to patient 202, the view 800 shows a current position 802 of the automated arm 514, position 804 of the first saved position, and a position 806 of the second saved position. The augmented reality component may include a display, such as display 311, electrically coupled to the controller for displaying graphical illustrations of the saved positions to the surgeon, which makes it much easier for the surgeon to recall and identify which saved position he wishes to choose. In another example, the augmented reality component may include a headset electrically coupled to the controller for displaying graphical illustrations of the saved positions to the surgeon. While a display and a headset are described as examples, any suitable device may be used to convey the information to the surgeon.

In another example, the controller may be configured to execute a redo command to return the automated arm 514 to the first position by loading the first saved position from the memory when an input is received from the input device corresponding to the redo command. In another example, the controller may be configured to execute the undo command to return the automated arm to a previous position from a subsequent position by performing previous movements in reverse even when the previous position has not been saved in response to receipt of an input corresponding to the undo command. In other words, the navigation system may automatically save some or all of previous positions in memory, at least temporarily, in case the surgeon wishes to revisit these positions at a later time. The redo and/or undo commands may be triggered with any suitable input, including through a graphical user interface, a foot pedal, or a voice command.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A medical navigation system including a surgical positioning system for positioning a payload during a medical procedure, the medical navigation system comprising:
   a robotic arm having a plurality of joints, the robotic arm forming part of the surgical positioning system and having an end effector for holding the payload;
   an input device for providing input; and
   a controller electrically coupled to the robotic arm and the input device, the controller having a processor coupled to a memory, the controller configured to perform the following during the medical procedure:
   position the robotic arm in a first position by providing a first positioning signal to the robotic arm;
   save the first position in the memory as a first saved position in response to a signal received from the input device;
   position the robotic arm in a second position by providing a second positioning signal to the robotic arm;
   return the robotic arm to the first position by loading the first saved position from the memory and providing the first positioning signal to the robotic arm when an input is received from the input device corresponding to a command to return to the first saved position;
   position the robotic arm in a third position by providing a third positioning signal to the robotic arm;
   save the third position in the memory as a second saved position in response to a signal received from the input device;
   position the robotic arm in a fourth position by providing a fourth positioning signal to the robotic arm;
   return the robotic arm to one of the first saved position and the second saved position by loading the corresponding first or second saved position from the memory when an input is received from the input device corresponding to a command to return to one of the first and second saved positions,
   wherein each of the first and second saved positions corresponds to a tool held by the end effector and the controller is further configured to automatically position the robotic arm in one of the first and second saved positions when the corresponding tool is placed in the end effector.

2. The medical navigation system according to claim 1, wherein the first saved position is defined by encoder joint angles for each of the plurality of joints.

3. The medical navigation system according to claim 1, wherein the input device includes at least one of a foot pedal, a microphone providing voice input, a touch sensitive overlay on the display, a mouse, and a keyboard.

4. The medical navigation system according to claim 1, wherein the payload includes at least one of a camera held by the end effector and electrically coupled to the controller and a surgical tool held by the end effector.

5. The medical navigation system according to claim 1, wherein the first position is manually positioned a first time based on input provided to the medical navigation system, including at least one of a surgeon physically moving the robotic arm to the first position and the surgeon moving the robotic arm to the first position by providing input using the input device.

6. The medical navigation system according to claim 1 further comprising a tracking system electrically coupled to the controller wherein the first saved position is defined relative to a position of a patient determined by the tracking system.

7. The medical navigation system according to claim 6, wherein the tracking system is selected from the group consisting of an optical tracking system having a camera for viewing optical tracking markers attached to the patient, a 3D scanning tracking system having a 3D scanner for tracking the patient, and an electromagnetic tracking system having an electromagnetic sensor for tracking electromagnetic markers on the patient.

8. The medical navigation system according to claim 1 further comprising an augmented reality component for providing a view of saved positions including the first saved position to a surgeon, thereby allowing the surgeon to easily select between saved positions.

9. The medical navigation system according to claim 8, wherein the augmented reality component includes a display electrically coupled to the controller for displaying graphical illustrations of the saved positions to the surgeon.

10. The medical navigation system according to claim 8, wherein the augmented reality component includes a headset communicating with the controller for displaying graphical illustrations of the saved positions to the surgeon.

11. The medical navigation system according to claim 1, wherein the controller is further configured to:
execute a redo command to return the robotic arm to the first position by loading the first saved position from the memory when an input is received from the input device corresponding to the redo command.

12. The medical navigation system according to claim 1, wherein the controller is further configured to, when an input is received from the input device corresponding to an undo command:
execute the undo command to return the robotic arm to a previous position from a subsequent position by performing previous movements in reverse even when the previous position has not been explicitly saved.

13. A method of positioning a payload during a medical procedure in a medical navigation system including a surgical positioning system, the medical navigation system having a robotic arm, an input device, and a controller, the robotic arm having a plurality of joints and forming part of the surgical positioning system and having an end effector for holding the payload, the controller having a processor coupled to a memory, the method comprising:
positioning the robotic arm in a first position;
saving the first position in the memory as a first saved position in response to a signal received from the input device;
positioning the robotic arm in a second position;
returning the robotic arm to the first position by loading the first saved position from the memory arm when an input is received from the input device corresponding to a command to return to the first saved position;
positioning the robotic arm in a third position by providing a third positioning signal to the robotic arm;
saving the third position in the memory as a second saved position in response to a signal received from the input device;
positioning the robotic arm in a fourth position by providing a fourth positioning signal to the robotic arm;
returning the robotic arm to one of the first saved position and the second saved position by loading the corresponding first or second saved position from the memory when an input is received from the input device corresponding to a command to return to one of the first and second saved positions,
wherein each of the first and second saved positions corresponds to a tool held by the end effector and the controller is further configured to automatically position the robotic arm in one of the first and second saved positions when the corresponding tool is placed in the end effector.

14. The method according to claim 13, wherein the first saved position is defined by encoder joint angles for each of the plurality of joints.

15. The method according to claim 13, wherein the input device includes at least one of a foot pedal, a microphone providing voice input, a touch sensitive overlay on a display, a mouse, and a keyboard.

16. The method according to claim 13, wherein the payload includes at least one of a camera held by the end effector and electrically coupled to the controller and a surgical tool held by the end effector.

17. The method according to claim 13, wherein the first position is manually positioned a first time based on input provided to the medical navigation system, including at least one of a surgeon physically moving the robotic arm to the first position and the surgeon moving the robotic arm to the first position by providing input using the input device.

* * * * *